United States Patent
Song et al.

(10) Patent No.: US 11,786,884 B2
(45) Date of Patent: Oct. 17, 2023

(54) SUPERABSORBENT POLYMERS BASED ON COPOLYMERS OF CHARGED MONOMERS AND NEUTRAL MONOMERS

(71) Applicants: Kimberly-Clark Worldwide, Inc., Neenah, WI (US); MCMASTER UNIVERSITY, Hamilton (CA)

(72) Inventors: Xuedong Song, Alpharetta, GA (US); Kaiyuan Yang, Cumming, GA (US); Todd Ryan Hoare, Ancaster (CA); Zohreh Jomeh Farsangi, Hamilton (CA)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 17/917,324

(22) PCT Filed: Apr. 30, 2020

(86) PCT No.: PCT/US2020/030613
§ 371 (c)(1),
(2) Date: Oct. 6, 2022

(87) PCT Pub. No.: WO2021/221641
PCT Pub. Date: Nov. 4, 2021

(65) Prior Publication Data
US 2023/0130584 A1    Apr. 27, 2023

(51) Int. Cl.
*B01J 20/26* (2006.01)
*B01J 20/28* (2006.01)
*B01J 20/30* (2006.01)
*B01J 20/32* (2006.01)

(52) U.S. Cl.
CPC ....... *B01J 20/267* (2013.01); *B01J 20/28004* (2013.01); *B01J 20/28016* (2013.01); *B01J 20/3021* (2013.01); *B01J 20/3078* (2013.01); *B01J 20/3221* (2013.01); *B01J 2220/68* (2013.01)

(58) Field of Classification Search
CPC .... B01J 20/26; B01J 20/267; B01J 20/28004; B01J 20/28016; B01J 20/3021; B01J 20/3078; B01J 20/3221; B01J 2220/68
USPC ....................................................... 502/402
See application file for complete search history.

(56) References Cited

U.S. PATENT DOCUMENTS

| | | |
|---|---|---|
| 5,250,640 A | 10/1993 | Irie et al. |
| 5,373,066 A | 12/1994 | Rebre et al. |
| 5,397,845 A | 3/1995 | Rebre et al. |
| 5,408,006 A | 4/1995 | Rebre et al. |
| 5,994,419 A | 11/1999 | Collette et al. |
| 8,871,880 B2 | 10/2014 | Naumann et al. |
| 9,353,007 B2 | 5/2016 | Eberwein et al. |
| 10,307,732 B2 | 6/2019 | Tian et al. |
| 2007/0135785 A1 | 6/2007 | Qin et al. |
| 2011/0095227 A1 | 4/2011 | Herth et al. |
| 2016/0108227 A1 | 4/2016 | Wattebled et al. |
| 2016/0177002 A1 | 6/2016 | Palchik et al. |

FOREIGN PATENT DOCUMENTS

| | | |
|---|---|---|
| EP | 0068189 A1 | 1/1983 |
| EP | 1553989 B1 | 3/2006 |
| JP | H0320314 A | 1/1991 |
| JP | H04246403 A | 9/1992 |
| JP | H05170835 A | 7/1993 |
| JP | 10555523 B2 | 8/1993 |
| JP | 2509087 B2 | 6/1996 |
| JP | H1081714 A | 3/1998 |
| JP | 2011525556 A | 9/2011 |
| WO | 2013007819 A1 | 1/2013 |

OTHER PUBLICATIONS

International Search Report and Written Opinion for Patent Application PCT/US2020/030613 dated Jan. 27, 2021; 13 pp.
Jassal, Manjeet et al., "Synthesis and Characterization of Sodium Acrylate and 2-Acrylamido-2-Methylpropane Sulphonate (AMPS) Copolymer Gels;" Fibers and Polymers 2004; vol. 5, No. 2, pp. 95-104.
Liu, Yang et al., "A Study of the Synthesis and Properties of AM/AMPS Copolymer as Superabsorbent;" Macromolecular Materials and Engineering 2004; vol. 289; pp. 1074-1078.
Meng, Ye L, "Synthesis and swelling property of superabsorbent starch grafted with acrylic acid/2-acrylamido-2-methyl-1-propanesulfonic acid;" J Sci Food Agric. 2017; Aug. 97; pp. 3831-3840.
Shi, Shuxian et al., "Preparation of acrylic acid and AMPS cointercalated layered double hydroxide and its application for superabsorbent;" Journal of Applied Polymer Science 2011; vol. 121, Issue 3, 2 pp.
International Preliminary Report on Patentability for Patent Application PCT/US2020/030613 dated Mar. 28, 2022; 5 pp.
PCT Third Party Observation for PCT Application PCT/US2020/030613 submitted Aug. 29, 2022; 13 pp.
Graham, Andrew T. et al., "Commercial Processes for the Manufacture of Superabsorbent Polymers;" Modern Superabsorbent Polymer Technology, Chapter 3, pp. 69-103; ISBN 0-471-19411-5.

*Primary Examiner* — Edward M Johnson
(74) *Attorney, Agent, or Firm* — Armstrong Teasdale LLP

(57) ABSTRACT

Superabsorbent polymers are made of copolymers including a major portion of low molecular weight monomers each individually including a backbone and a charged moiety, a minor portion of high molecular weight monomers each individually including a backbone and a charged moiety, and optionally a crosslinker. The copolymer-based superabsorbent polymers have significantly improved absorbency under load.

10 Claims, No Drawings

SUPERABSORBENT POLYMERS BASED ON COPOLYMERS OF CHARGED MONOMERS AND NEUTRAL MONOMERS

CROSS-REFERENCE TO RELATED APPLICATIONS

This application is a U.S. National Phase Application of International Patent Application No. PCT/US2020/030613, filed Apr. 30, 2020, the contents of which are hereby expressly incorporated by reference in their entirety.

FIELD OF DISCLOSURE

This disclosure is directed to superabsorbent polymers that are made of copolymers of multiple charged monomers, where the charged moieties of different charged monomers have different distances from copolymer backbones. The copolymer-based superabsorbent polymers have significantly improved absorbency under load. Compositions and methods in accordance with the present disclosure are useful in a variety of absorbent products.

BACKGROUND

Superabsorbent polymers (SAPs) are three-dimensional networks that can absorb and retain water (or other aqueous media) and physiological fluids such as urine and blood more than hundreds times of their own dry weight, typically depending on the ionic concentration of the aqueous solution. SAPs have applications in a variety of fields, including medicine, personal care products, biomaterials, biosorbents, and agriculture. The first commercial SAPs were produced in 1970 through the alkaline hydrolysis of starch-g-polyacrylonitrile. While these polymers could absorb up to 500 gig of water, they were mechanically weak in their swollen state. SAPs were industrially developed in Japan and USA in the early 1980s for hygienic applications. It was found that SAPs had the potential to replace fluff, making their use in hygienic products such as baby diapers and feminine napkins cost effective.

Desired features of SAPs include high absorption capacity, high and tunable swelling rate, high absorbency under load, good strength of the swollen gel, high gel fraction after crosslinking, excellent durability and stability upon swelling and during storage, non-toxicity, and low cost. Although current hydrogel systems offer good performance in several of these different aspects, several drawbacks exist with various formulations, including low absorbency under pressure, gel blockage (by which the initial layer of SAP forms a relatively impermeable barrier to subsequent water diffusion and uptake deeper into the material), and high sensitivity to the electrolyte solutions. Various strategies have been employed to address these challenges, including forming composite and nanocomposite hydrogels, interpenetrating polymer network (IPN) hydrogels, and various surface treatments; however, improvements are still required to enable the use of minimal material in a broadest possible range of applications.

The nature of monomers and crosslinkers, their concentrations, and molar ratios are known as the most significant factors influencing the absorption capacity of a SAP. Acrylic acid, acrylamide and methacrylic acid are the most extensively-used monomers to prepare SAPs commercially. However, the potential presence of some residual acrylamide in the gels poses a challenge in the practical use of such hydrogels for human health and personal care products. Conversely, the water absorbing and swelling properties of ionic SAPs (e.g. based on acrylic acid or methacrylic acid) are substantially decreased in salt-containing liquids, including physiological fluids like urine and blood. The reason for this salt sensitivity is that the counterions such as sodium ions ($Na^+$) present in physiological fluids can effectively screen the polymer backbone charges, resulting in counterion condensation with polymer-bound charged groups and, consequently, reduced counterion entropy and direct chain-chain repulsion forces available to drive a swelling response.

A number of strategies have been developed for SAPs to attempt to address some of these challenges.

As a representative example of approaches in the area of zwitterionic copolymer SAPs. Kabiri et al. reported the synthesis of hydrogels based on the zwitterionic monomer [3-(methacrylamido) propyl] dimethyl (3-sulfopropyl) ammonium hydroxide (MPDSAH) and 2-acrylamido-2-methylpropane sulfonic acid (AMPS) through solution polymerization (Kabiri et al., *Polym Adv Technol* 2005; 16, 659-666). Free swelling in water was increased from 2.3 g/g for the AMPS-free sample to a maximum swelling of 212.3 g/g with 20 mol % AMPS, above which swelling was again depressed. In 0.9% saline solution the lowest swelling 12.6 g/g corresponded to the AMPS-free sample, with swelling increasing to 32.8 g/g upon incorporation of 20 mol % AMPS. Due to the zwitterionic nature of the SAP, the swelling of the hydrogels is relatively pH independent over a wide range of pH values; similar near-constant swelling was also observed in environments with various ionic strengths. However, the absorbance under load (AUL) was not measured and using a zwitterionic monomer as the primary monomer would introduce substantially higher costs to producing SAPs for commercial products.

As a representative example of approaches in the area of nanocomposite SAPs, Chen et al. synthesized superabsorbent hydrogels by solution copolymerization of partially neutralized acrylic acid and AMPS in the presence of the hydrophilic nano-sized clay Laponite XLG to improve the shape stability and mechanical properties of the gels (Chen et al., *Appl Mech Mater* 2013; 427-429: 364-367). Free swelling was observed to increase significantly with the increase of AMPS, with the free swelling ratio increasing from 460 g/g dried gel for AA-only hydrogels to 750 g/g dried gel when the mole ratio of AMPS:AA was 1. Further small improvements in water binding as well as substantial improvements in gel shape stability were observed upon the incorporation of clay up to 20 mol % total monomer content, consistent with a balance between adding a highly charged and hygroscopic filler (increased sorption capacity) and introducing physical crosslinks into the system (decreased sorption capacity). However, the interactions between nanoscale fillers and bulk gels are challenging to engineer, with the balance between higher gel-filler interactions (increased physical crosslinking and thus reduced swelling) and lower gel-filler interactions (filler aggregation) critical to control to achieve the desired combination of higher strength and high swelling.

It is known that saline-absorbency under load (AUL) can be improved through surface crosslinking reactions between the functional groups of SAPs and suitable surface crosslinking agents. Surface crosslinking helps improve the local mechanics of the SAP particles at the particle surface while also reducing the "gel blockage" often observed with swollen particles that poses a transport challenge for water to access the SAP deeper within the SAP mat. Generally, higher crosslinking densities at the surface of SAP particles impart better AUL properties. Bifunctional compounds like diglycidyls and diols are mostly employed for the SAP surface treatment. Epoxy silane compounds, such as 3-glycidopropoxytrimethoxy silane (GPS) have been also used for surface modification of SAPs. This compound can increase the AUL through two mechanisms: reaction of carboxylic acid with the epoxy group of GPS and oligomerization of siloxanes on the SAP particle surface. However, surface crosslinking introduces an additional processing step and can increase the amount of leachable compounds from SAPs unless the residual crosslinker is thoroughly removed from the hydrogels.

It is also known that multifunctional crosslinkers can be used not only enhance mechanical strength but also introduce other advantages to the SAP owing to their branched structures. For example, Ghasri et al. synthesized glycerol-lactic acid-based star-shaped modifier (SM) for the surface modification of hygienic SAP hydrogels to increase the saline-AUL and the swollen gel strength. Implementing the surface treatment led to an AUL increase of up to 28% in the modified SAP (M. Ghasri et al., *Polym Adv Technol.*, 2018; 1-10). The modified samples showed lower salt sensitivity factor (f) in NaCl (f=0.7) and $CaCl_2$ (f=0.93-0.95) compared with the intact SAP (f=0.84 for NaCl, and f=0.95-0.97 for $CaCl_2$), attributed to the chelating effect induced by such multi-functional modifiers. Deionized water free swelling capacity of the intact SAP was approximately 366 g/g; however, surface crosslinking of the SAPs with $S_{11}$ (SMs containing one LA molecule in each arm) led to a reduction in the $Q_{DW}$ values (decreased to 249 and 219 g/g using 0.5 g and 1.5 g of the crosslinker, respectively). Thus, surface crosslinking with branched crosslinkers improved the AUL but not the free water binding capacity of the hydrogel. The branched crosslinkers are also synthetically more complex and expensive to prepare, a key consideration for commodity use applications in a disposable product such as sanitary pads or diapers.

As an alternative to these strategies, the present work discloses rational engineering of the structures of the polymers comprising SAPs to optimize the number of residues in the SAPs that are ionized and thus can induce Donnan equilibrium/direct chain repulsion.

Conventional superabsorbent materials (SAMs) are mainly made of two classes of polymers: synthetic polymers and natural polymers. In general, synthetic superabsorbent polymers are charged polyelectrolytes such as salts of polyacrylic acid (PAA), polyvinyl sulfonic acid, polyvinyl phosphoric acid, and partially hydrolyzed maleic anhydride copolymers. Natural polymers include both neutral and charged polymers such as carboxymethylcellulose, sodium alginate, chitosan salt and modified starch. All these known SAMs have substantial limitations. For instance, the most widely used commercial PAA-based SAMs have limited absorbency under load (AUL) and are also very salt-sensitive.

Conventional wisdom is that AULs of SAMs based on polymers of lower-molecular weight charged monomers should be higher than SAMs that are based on larger molecular weight-based charged monomers.

In the present disclosure, it was surprisingly found that only a small portion of the total mass (<20%) in PAA-based SAM particles contributes significantly to the osmotic pressure and electric repulsion that are the major positive driving forces for SAM swelling under load. Those non-neutralized acrylic acid monomers (AA) and neutralized acrylate sodium salts in an ion pair state for PAA-based SAM particles do not contribute significantly to osmotic pressure and electric repulsion.

It was also surprisingly found that a low degree of ionization is present within AA-based SAPs (7-8%) even at pH values in which "full" effective ionization is anticipated. Such lower ionization levels significantly limit the ultimate water content and thus the efficacy of conventional AA-based SAPs. As such, ionization and thus improved swelling may be achievable by varying the type of charge present as well as the spacing of the charges present (both between charged monomer residues within the constituent polymer chains as well as the between the backbone and the charge on individual monomer residues)

It was further surprisingly found that AULs of SAMs that are based on copolymers of different charged monomers depend significantly upon the distance between the charged centers and polymer backbones.

These findings are applicable to a variety of homo-polyelectrolyte-based SAM systems. Homopolyelectrolyte-based SAMs are very sensitive to salts, which results in lower absorbency for aqueous liquids containing high concentration of salts.

Described herein are SAMs that are made of copolymers of multiple charged monomers where the charged moieties of different charged monomers have different distances from copolymer backbones. The copolymer-based SAM particles have significantly improved absorbency under load.

Compositions and methods in accordance with the present disclosure are useful in a variety of absorbent products.

Objective of the Disclosure

The aim of the present disclosure is to address the low ionization levels of AA-based SAPs by using free radical polymerization techniques to copolymerize minor portions of different hydrophilic comonomers into the AA-based SAP backbone. Such comonomers serve to rationally engineer the ionization state of the remaining AA residues by physically spacing the ionizable monomers apart, and thus reducing the polyelectrolyte effect in which the ionization of an adjacent charged residue increases the effective $pK_a$ of the remaining uncharged residue.

BRIEF DESCRIPTION OF THE DISCLOSURE

In one aspect, provided herein is a superabsorbent polymer comprising
a copolymer comprising
a major portion of low molecular weight monomers each individually comprising
a backbone and a charged moiety;
a minor portion of high molecular weight monomers each individually comprising a backbone and a charged moiety; and
optionally a crosslinker;
wherein the average distance between the backbone and charged moiety of each individual low molecular weight monomer is less than the average distance between the backbone and charged moiety of each individual high molecular weight monomer.

In another aspect, provided herein is a method of making a superabsorbent polymer comprising
a copolymer comprising
a major portion of low molecular weight monomers each individually comprising a backbone and a charged moiety;
a minor portion of high molecular weight monomers each individually comprising a backbone and a charged moiety; and optionally a crosslinker;
wherein the average distance between the backbone and charged moiety of each individual low molecular weight monomer is less than the average distance between the backbone and charged moiety of each individual high molecular weight monomer, the method comprising
forming a mixture comprising
a solvent
a low molecular weight monomer comprising a backbone and a charged moiety;
a high molecular weight monomer comprising a backbone and a charged moiety; and
optionally a crosslinker
initiating a reaction; and
reacting the mixture.

In yet another aspect, provided herein is a method of using a superabsorbent polymer comprising
a copolymer comprising
a major portion of low molecular weight monomers each individually comprising a backbone and a charged moiety;
a minor portion of high molecular weight monomers each individually comprising a backbone and a charged moiety; and
optionally a crosslinker;
wherein the average distance between the backbone and charged moiety of each individual low molecular weight monomer is less than the average distance between the backbone and charged moiety of each individual high molecular weight monomer, the method comprising using the superabsorbent polymer in a consumer product.

DETAILED DESCRIPTION OF THE DISCLOSURE

Superabsorbent polymers according to the present disclosure comprise a copolymer comprising a major portion of low molecular weight monomers each individually comprising a backbone and a charged moiety, a minor portion of high molecular weight monomers each individually comprising a backbone and a charged moiety, and optionally a crosslinker. The average distance between the backbone and charged moiety of each individual low molecular weight monomer is less than the average distance between the backbone and charged moiety of each individual high molecular weight monomer.

In some embodiments, the copolymer comprises two or more different species of monomers. In some embodiments, the copolymer comprises three or more different species of monomers. In some embodiments, the copolymer comprises four or more different species of monomers. In some embodiments, the copolymer comprises five or more different species of monomers. In some embodiments, the copolymer comprises six or more different species of monomers.

In some embodiments, the copolymer comprises one or more different species of low molecular weight monomers. In some embodiments, the copolymer comprises two or more different species of low molecular weight monomers. In some embodiments, the copolymer comprises three or more different species of low molecular weight monomers.

In some embodiments, the copolymer comprises one or more different species of high molecular weight monomers. In some embodiments, the copolymer comprises two or more different species of high molecular weight monomers. In some embodiments, the copolymer comprises three or more different species of high molecular weight monomers.

In some embodiments, the copolymer lacks structured ordering of the low molecular weight monomers and the high molecular weight monomers. In some embodiments, the copolymer is as random as possible. In some embodiments, the probability of finding a given type of monomer residue at a particular point along the polymer backbone is about equal to the mole fraction of that monomer residue in the polymer backbone.

In some embodiments, the copolymer does not comprise a block copolymer of the low molecular weight monomers and the high molecular weight monomers. In some embodiments, the copolymer does not comprise an alternating copolymer of the low molecular weight monomers and the high molecular weight monomers. In some embodiments, the copolymer does not comprise a graft copolymer of the low molecular weight monomers and the high molecular weight monomers.

In some embodiments, the major portion is present in an amount greater than about 50 mol %, greater than about 51 mol %, greater than about 52 mol %, greater than about 53 mol %, greater than about 54 mol %, greater than about 55 mol %, greater than about 56 mol %, greater than about 57 mol %, greater than about 58 mol %, greater than about 59 mol %, greater than about 60 mol %, greater than about 61 mol %, greater than about 62 mol %, greater than about 63 mol %, greater than about 64 mol %, greater than about 65 mol %, greater than about 66 mol %, greater than about 67 mol %, greater than about 68 mol %, greater than about 69 mol %, greater than about 70 mol %, greater than about 71 mol %, greater than about 72 mol %, greater than about 73 mol %, greater than about 74 mol %, greater than about 75 mol %, greater than about 76 mol %, greater than about 77 mol %, greater than about 78 mol %, greater than about 79 mol %, greater than about 80 mol %, greater than about 81 mol %, greater than about 82 mol %, greater than about 83 mol %, greater than about 84 mol %, greater than about 85 mol %, greater than about 86 mol %, greater than about 87 mol %, greater than about 88 mol %, or greater than about 89 mol % of the copolymer, greater than about 90 mol %, greater than about 91 mol %, greater than about 92 mol %, greater than about 93 mol %, greater than about 94 mol %, or greater than about 95 mol % of the copolymer.

In some embodiments, the major portion is present in an amount greater than about 60 mol % of the copolymer.

In some embodiments, the minor portion is present in an amount greater than about 5 mol %, greater than about 6 mol %, greater than about 7 mol %, greater than about 8 mol %, greater than about 9 mol %, greater than about 10 mol %, greater than about 11 mol %, greater than about 12 mol %, greater than about 13 mol %, greater than about 14 mol %, greater than about 15 mol %, greater than about 16 mol %, greater than about 17 mol %, greater than about 18 mol %, greater than about 19 mol %, greater than about 20 mol %, greater than about 21 mol %, greater than about 22 mol %, greater than about 23 mol %, greater than about 24 mol %, greater than about 25 mol %, greater than about 26 mol %, greater than about 27 mol %, greater than about 28 mol %, greater than about 29 mol %, greater than about 30 mol %, greater than about 31 mol %, greater than about 32 mol %, greater than about 33 mol %, greater than about 34 mol %, greater than about 35 mol %, greater than about 36 mol %, greater than about 37 mol %, greater than about 38 mol %, greater than about 39 mol %, greater than about 40 mol %, greater than about 41 mol %, greater than about 42 mol %, greater than about 43 mol %, greater than about 44 mol %, greater than about 45 mol %, greater than about 46 mol %, greater than about 47 mol %, greater than about 48 mol %, or greater than about 49 mol % of the copolymer.

In some embodiments, the minor portion is present in an amount less than about 5 mol %, less than about 6 mol %, less than about 7 mol %, less than about 8 mol %, less than about 9 mol %, less than about 10 mol %, less than about 10 mol %, less than about 11 mol %, less than about 12 mol %, less than about 13 mol %, less than about 14 mol %, less than about 15 mol %, less than about 16 mol %, less than about 17 mol %, less than about 18 mol %, less than about 19 mol %, less than about 20 mol %, less than about 21 mol %, less than about 22 mol %, less than about 23 mol %, less than about 24 mol %, less than about 25 mol %, less than about 26 mol %, less than about 27 mol %, less than about 28 mol %, less than about 29 mol %, less than about 30 mol %, less than about 31 mol %, less than about 32 mol %, less than about 33 mol %, less than about 34 mol %, less than about 35 mol %, less than about 36 mol %, less than about 37 mol %, less than about 38 mol %, less than about 39 mol %, less than about 40 mol %, less than about 41 mol %, less than about 42 mol %, less than about 43 mol %, less than about 44 mol %, less than about 45 mol %, less than about 46 mol %, less than about 47 mol %, less than about 48 mol %, or less than about 49 mol % of the copolymer.

In some embodiments, the minor portion is present in an amount less than about 40 mol % of the copolymer.

In some embodiments, the major portion is present in an amount greater than about 50 mol % of the copolymer and the minor portion is present in an amount less than about 50 mol % of the copolymer. In some embodiments, the major portion is present in an amount greater than about 55 mol % of the copolymer and the minor portion is present in an amount less than about 45 mol % of the copolymer. In some embodiments, the major portion is present in an amount greater than about 60 mol % of the copolymer and the minor portion is present in an amount less than about 40 mol % of the copolymer. In some embodiments, the major portion is present in an amount greater than about 65 mol % of the copolymer and the minor portion is present in an amount less than about 35 mol % of the copolymer. In some embodiments, the major portion is present in an amount greater than about 70 mol % of the copolymer and the minor portion is present in an amount less than about 30 mol % of the copolymer. In some embodiments, the major portion is present in an amount greater than about 75 mol % of the copolymer and the minor portion is present in an amount less than about 25 mol % of the copolymer. In some embodiments, the major portion is present in an amount greater than about 80 mol % of the copolymer and the minor portion is present in an amount less than about 20 mol % of the copolymer. In some embodiments, the major portion is present in an amount greater than about 85 mol % of the copolymer and the minor portion is present in an amount less than about 15 mol % of the copolymer. In some embodiments, the major portion is present in an amount greater than about 90 mol % of the copolymer and the minor portion is present in an amount less than about 10 mol % of the copolymer. In some embodiments, the major portion is present in an amount greater than about 95 mol % of the copolymer and the minor portion is present in an amount less than about 5 mol % of the copolymer.

In some embodiments, the major portion is present in an amount greater than about 60 mol % of the copolymer and the minor portion is present in an amount less than about 40 mol % of the copolymer.

In some embodiments, the superabsorbent polymer is in a form selected from the group consisting of a particle, a gel, a fiber, a bead, a liquid, a solid, a paste, or combinations thereof. In some embodiments, the superabsorbent polymer is a gel. In some embodiments, the superabsorbent polymer is a particle.

In some embodiments, the superabsorbent polymer is in a form with a diameter in the range of about 100 µm to about 1000 µm, about 100 µm to about 900 µm, about 100 µm to about 800 µm, about 100 µm to about 700 µm, about 100 µm to about 600 µm, about 100 µm to about 500 µm, about 100 µm to about 400 µm, about 100 µm to about 300 µm, or about 100 µm to about 200 µm. In some embodiments, the superabsorbent polymer is in a form with a diameter in the range of about 200 µm to about 900 µm, about 300 µm to about 800 µm, about 400 µm to about 700 µm, or about 500 µm to about 600 µm.

In some embodiments, the superabsorbent polymer is in a form with a diameter in the range of about 300 µm to about 600 µm.

In some embodiments, the superabsorbent polymer is a particle with a diameter in the range of about 100 µm to about 1000 µm. In some embodiments, the superabsorbent polymer is a particle with a diameter in the range of about 300 µm to about 600 µm.

In some embodiments, the superabsorbent polymer does not comprise a crosslinker. In some embodiments, the superabsorbent polymer comprises one or more cross-linkers. In some embodiments, the superabsorbent polymer comprises two or more cross-linkers.

In some embodiments, the superabsorbent polymer comprises a crosslinker selected from the group consisting of methylene(bis) acrylamide (MBAA), poly(ethylene glycol) diacrylate) (PEGDA), ethylene glycol diacrylate (EGDA), ethylene glycol dimethacrylate (EGDMA), poly(ethylene glycol dimethacrylate) (PEGDMA), and combinations thereof.

In some embodiments, the superabsorbent polymer is lightly crosslinked. In some embodiments, the superabsorbent polymer has a crosslinker density in the range of about 0.1 mol % to about 1 mol %. In some embodiments, the superabsorbent polymer has a crosslinker density in the range of about 0.2 mol % to about 1 mol %.

In some embodiments, the superabsorbent polymer is surface-crosslinked.

In some embodiments, the average distance between the backbone and charged moiety of each individual low molecular weight monomer is less than about 5 angstroms. In some embodiments, the average distance between the backbone and charged moiety of each individual low molecular weight monomer is less than about 4.5 angstroms. In some embodiments, the average distance between the backbone and charged moiety of each individual low molecular weight monomer is less than about 4.0 angstroms. In some embodiments, the average distance between the backbone and charged moiety of each individual low molecular weight monomer is less than about 3.5 angstroms. In some embodiments, the average distance between the backbone and charged moiety of each individual low molecular weight monomer is less than about 3.0 angstroms. In some embodiments, the average distance between the backbone and charged moiety of each individual low molecular weight monomer is less than about 2.5 angstroms. In some embodiments, the average distance between the backbone and charged moiety of each individual low molecular weight monomer is less than about 2.0 angstroms. In some embodiments, the average distance between the backbone and charged moiety of each individual low molecular weight monomer is less than about 1.5 angstroms.

In some embodiments, the average distance between the backbone and charged moiety of each individual high molecular weight monomer is greater than about 5 angstroms. In some embodiments, the average distance between the backbone and charged moiety of each individual high molecular weight monomer is greater than about 5.5 angstroms. In some embodiments, the average distance between the backbone and charged moiety of each individual high molecular weight monomer is greater than about 6 angstroms. In some embodiments, the average distance between the backbone and charged moiety of each individual high molecular weight monomer is greater than about 6.5 angstroms. In some embodiments, the average distance between the backbone and charged moiety of each individual high molecular weight monomer is greater than about 7 angstroms. In some embodiments, the average distance between the backbone and charged moiety of each individual high molecular weight monomer is greater than about 7.5 angstroms. In some embodiments, the average distance between the backbone and charged moiety of each individual high molecular weight monomer is greater than about 8 angstroms. In some embodiments, the average distance between the backbone and charged moiety of each individual high molecular weight monomer is greater than about 8.5 angstroms. In some embodiments, the average distance between the backbone and charged moiety of each individual high molecular weight monomer is greater than about 9 angstroms. In some embodiments, the average distance between the backbone and charged moiety of each individual high molecular weight monomer is greater than about 9.5 angstroms. In some embodiments, the average distance between the backbone and charged moiety of each individual high molecular weight monomer is greater than about 10 angstroms.

In some embodiments, the average distance between the backbone and charged moiety of each individual low molecular weight monomer is less than about 5 angstroms and the average distance between the backbone and charged moiety of each individual high molecular weight monomer is greater than about 5 angstroms.

In some embodiments, the major portion of low molecular weight monomers each individually comprising a backbone and a charged moiety comprises a low molecular weight monomer having a molecular weight less than about 150 g/mol. In some embodiments, the major portion of low molecular weight monomers each individually comprising a backbone and a charged moiety comprises a low molecular weight monomer having a molecular weight less than about 125 g/mol. In some embodiments, the major portion of low molecular weight monomers each individually comprising a backbone and a charged moiety comprises a low molecular weight monomer having a molecular weight less than about 100 g/mol. In some embodiments, the major portion of low molecular weight monomers each individually comprising a backbone and a charged moiety comprises a low molecular weight monomer having a molecular weight less than about 75 g/mol. In some embodiments, the major portion of low molecular weight monomers each individually comprising a backbone and a charged moiety comprises a low molecular weight monomer having a molecular weight less than about 50 g/mol. In some embodiments, the major portion of low molecular weight monomers each individually comprising a backbone and a charged moiety comprises a low molecular weight monomer having a molecular weight less than about 25 g/mol.

In some embodiments, the minor portion of high molecular weight monomers each individually comprising a backbone and a charged moiety comprises a high molecular weight monomer having a molecular weight greater than about 150 g/mol. In some embodiments, the minor portion of high molecular weight monomers each individually comprising a backbone and a charged moiety comprises a high molecular weight monomer having a molecular weight greater than about 200 g/mol. In some embodiments, the minor portion of high molecular weight monomers each individually comprising a backbone and a charged moiety comprises a high molecular weight monomer having a molecular weight greater than about 250 g/mol. In some embodiments, the minor portion of high molecular weight monomers each individually comprising a backbone and a charged moiety comprises a high molecular weight monomer having a molecular weight greater than about 300 g/mol. In some embodiments, the minor portion of high molecular weight monomers each individually comprising a backbone and a charged moiety comprises a high molecular weight monomer having a molecular weight greater than about 350 g/mol. In some embodiments, the minor portion of high molecular weight monomers each individually comprising a backbone and a charged moiety comprises a high molecular weight monomer having a molecular weight greater than about 400 g/mol. In some embodiments, the minor portion of high molecular weight monomers each individually comprising a backbone and a charged moiety comprises a high molecular weight monomer having a molecular weight greater than about 450 g/mol. In some embodiments, the minor portion of high molecular weight monomers each individually comprising a backbone and a charged moiety comprises a high molecular weight monomer having a molecular weight greater than about 500 g/mol.

In some embodiments, the major portion of low molecular weight monomers each individually comprising a backbone and a charged moiety comprises a low molecular weight monomer having a molecular weight less than about 150 g/mol and the minor portion of high molecular weight monomers each individually comprising a backbone and a charged moiety comprises a high molecular weight monomer having a molecular weight greater than about 150 g/mol.

In some embodiments, the major portion of low molecular weight monomers each individually comprising a backbone and a charged moiety comprises a low molecular weight monomer having 1, 2, 3, 4, or 5 carbon atoms. In some embodiments, the major portion of low molecular weight monomers each individually comprising a backbone and a charged moiety comprises a low molecular weight monomer having 3, 4, or 5 carbon atoms. In some embodiments, the major portion of low molecular weight monomers each individually comprising a backbone and a charged moiety comprises a low molecular weight monomer having 1, 2, 3, or 4 oxygen atoms. In some embodiments, the major portion of low molecular weight monomers each individually comprising a backbone and a charged moiety comprises a low molecular weight monomer having 2, 3, or 4 oxygen atoms.

In some embodiments, the minor portion of high molecular weight monomers each individually comprising a backbone and a charged moiety comprises a high molecular weight monomer having 6, 7, 8, 9, 10, 11, 12, 13, 14, 15, 16, 17, 18, 19, or 20 carbon atoms. In some embodiments, the minor portion of high molecular weight monomers each individually comprising a backbone and a charged moiety comprises a high molecular weight monomer having 1, 2, 3, 4, 5, 6, 7, 8, 9, or 10 oxygen atoms. In some embodiments, the minor portion of high molecular weight monomers each individually comprising a backbone and a charged moiety comprises a high molecular weight monomer having 2, 3, 4, 5, 6, 7, 8, 9, or 10 oxygen atoms.

In some embodiments, the major portion of low molecular weight monomers each individually comprising a backbone and a charged moiety comprises a low molecular weight monomer having a net negative charge. In some embodiments, the major portion of low molecular weight monomers each individually comprising a backbone and a charged moiety comprises a low molecular weight monomer having a net positive charge.

In some embodiments, the major portion of low molecular weight monomers each individually comprising a backbone and a charged moiety comprises a low molecular weight monomer having one negative or positive charge. In some embodiments, the major portion of low molecular weight monomers each individually comprising a backbone and a charged moiety comprises a low molecular weight monomer having two negative or positive charges.

In some embodiments, the minor portion of high molecular weight monomers each individually comprising a backbone and a charged moiety comprises a high molecular weight monomer having a net negative charge. In some embodiments, the minor portion of high molecular weight monomers each individually comprising a backbone and a charged moiety comprises a high molecular weight monomer having a net positive charge.

In some embodiments, the copolymer comprises low molecular weight monomers and high molecular weight monomers with the same amount of negative charges. In some embodiments, the copolymer comprises low molecular weight monomers and high molecular weight monomers, wherein the low molecular weight monomers have more negative charges than the high molecular weight monomers. In some embodiments, the copolymer comprises low molecular weight monomers and high molecular weight monomers, wherein the low molecular weight monomers have less negative charges than the high molecular weight monomers.

In some embodiments, the minor portion of high molecular weight monomers each individually comprising a backbone and a charged moiety comprises a high molecular weight monomer that is selected from the group consisting of 2-acrylamido-2-methylpropane sulfonic acid, 3-sulfopropyl methacrylate potassium salt, 3-sulfopropyl acrylate potassium salt, acrylate or methacrylate monomers with tethered sulfate groups and salts thereof, salts of vinyl-linker-acid units, salts of vinyl-linker-acid units where the linker has a length of at least 3 angstroms, vinylic sulfate monomers, and combinations thereof.

In some embodiments, the major portion of low molecular weight monomers each individually comprising a backbone and a charged moiety comprises a low molecular weight monomer that is selected from the group consisting of acrylic acids, methacrylic acids, vinyl sulfonic acids, vinyl phosphoric acids, partially hydrolyzed maleic anhydrides, and combinations thereof.

In some embodiments, the copolymer does not comprise a zwitterionic charged monomer. In some embodiments, the copolymer does not comprise a nonionic monomer.

In some embodiments, the copolymer is synthesized according to a method selected from the group consisting of free radical polymerization, anionic polymerization, controlled radical polymerization methods, atom-transfer radical-polymerization (ATRP), nitroxide mediated radical polymerization (NMP), reversible addition-fragmentation chain-transfer polymerization (RAFT), and combinations thereof. In some embodiments, the copolymer is synthesized according to free radical polymerization.

In some embodiments, the free radicals may be generated by photolysis, thermal decomposition, or ambient redox conditions.

In some embodiments, the copolymer is synthesized according to a method comprising forming a mixture comprising a solvent, a low molecular weight monomer comprising a backbone and a charged moiety, a high molecular weight monomer comprising a backbone and a charged moiety, and optionally a crosslinker; initiating a reaction; and reacting the mixture.

In some embodiments, the method step of initiating a reaction comprises adding an initiator, an accelerator, or a combination thereof to the mixture. In some embodiments, the initiator is an oxidizing agent.

In some embodiments, the initiator is an organic compound. In some embodiments, the initiator is selected from the group consisting of azo compounds, organic peroxide compounds, organic persulfate compounds, and combinations thereof. In some embodiments, the initiator is an azo compound. In some embodiments, the initiator is an organic peroxide compound. In some embodiments, the initiator is an organic persulfate compound.

In some embodiments, the initiator is an inorganic compound. In some embodiments, the initiator is selected from the group consisting of inorganic peroxide compounds, metal reductants, iron, chromium, vanadium, titanium, cobalt, copper, and combinations thereof. In some embodiments, the initiator is an inorganic peroxide compound. In some embodiments, the initiator is selected from the group consisting of potassium persulfate, ammonium persulfate, and combinations thereof. In some embodiments, the reduction of hydrogen peroxide or an alkyl hydrogen peroxide can happen by iron or other reductants such as $Cr^{2+}$, $V^{2+}$, $Ti^{3+}$, $Co^{2+}$, or $Cu^+$.

In some embodiments, the initiator is an oxidizing agent. In some embodiments, the initiator is a persulfate. In some embodiments, the initiator is selected from the group consisting of potassium persulfate, ammonium persulfate, and combinations thereof.

In some embodiments, the accelerator is an organic compound. In some embodiments, the accelerator is an organic base. In some embodiments, the accelerator is tetramethylethylenediamine (TEMED). In other embodiments, the accelerator is sodium metabisulfite (SPS). In some embodiments, no accelerator is used. In some embodiments, the accelerator is selected from the group consisting of organic compounds, organic bases, TEMED, SPS, no accelerator, and combinations thereof.

In some embodiments, the method step of reacting the mixture comprises reacting the mixture in an inert atmosphere. In some embodiments, the method step of reacting the mixture comprises reacting the mixture in a static inert atmosphere. In some embodiments, the method step of reacting the mixture comprises reacting the mixture in a dynamic inert atmosphere. In some embodiments, the method step of reacting the mixture comprises reacting the mixture under a flow of an inert gas.

In some embodiments, the method step of reacting the mixture comprises reacting the mixture in an inert atmosphere selected from the group consisting of $N_2$, $CO_2$, noble gases, helium, neon, argon, krypton, xenon, and a combination thereof. In some embodiments, the method step of reacting the mixture comprises reacting the mixture in an inert atmosphere of $N_2$.

In some embodiments, the method step of reacting the mixture comprises heating the mixture. In some embodiments, the method step of reacting the mixture comprises heating the mixture to a temperature in the range of about 20° C. to about 100° C. In some embodiments, the method step of reacting the mixture comprises heating the mixture to a temperature in the range of about 30° C. to about 100° C. In some embodiments, the method step of reacting the mixture comprises heating the mixture to a temperature in the range of about 40° C. to about 100° C. In some embodiments, the method step of reacting the mixture comprises heating the mixture to a temperature in the range of about 50° C. to about 100° C. In some embodiments, the method step of reacting the mixture comprises heating the mixture to a temperature in the range of about 60° C. to about 100° C. In some embodiments, the method step of reacting the mixture comprises heating the mixture to a temperature in the range of about 70° C. to about 100° C.

In some embodiments, the method step of reacting the mixture comprises heating the mixture to a temperature in the range of about 20° C. to about 90° C. In some embodiments, the method step of reacting the mixture comprises heating the mixture to a temperature in the range of about 30° C. to about 80° C. In some embodiments, the method step of reacting the mixture comprises heating the mixture to a temperature in the range of about 40° C. to about 70° C.

In some embodiments, the method step of reacting the mixture comprises heating the mixture to a temperature in the range of about 20° C. to about 40° C. In some embodiments, the method step of reacting the mixture comprises heating the mixture to about 40° C. In some embodiments, the method step of reacting the mixture comprises heating the mixture to about 70° C.

In some embodiments, the method further comprises drying the reaction product. In some embodiments, the method further comprises drying the reaction product in an oven. In some embodiments, the method further comprises drying the reaction product at a temperature in the range of about 50° C. to about 100° C. In some embodiments, the method further comprises drying the reaction product at a temperature in the range of about 60° C. to about 100° C. In some embodiments, the method further comprises drying the reaction product at a temperature in the range of about 70° C. to about 100° C. In some embodiments, the method further comprises drying the reaction product at a temperature in the range of about 80° C. to about 100° C. In some embodiments, the method further comprises drying the reaction product at a temperature in the range of about 60° C. to about 90° C. In some embodiments, the method further comprises drying the reaction product at a temperature in the range of about 70° C. to about 90° C.

In some embodiments, the method further comprises drying the reaction product at a temperature of about 85° C.

In some embodiments, the method further comprises grinding the reaction product. In some embodiments, the method further comprises grinding the reaction product with a grinding device selected from the group consisting of a mechanical blender, coffee grinder, a crusher, a pulveriser, a grinder, a mill, and combinations thereof.

In some embodiments, the ability of a polymer to absorb fluid under a static load can be measured as absorbance under load (AUL). A typical AUL test format may be used.

In some embodiments, the capacity of a pre-swollen polymer to retain water under force can be measured as centrifuge retention capacity (CRC). A typical CRC test format may be used.

In some embodiments, the superabsorbent polymer is used in a consumer product or a superabsorbent material. In some embodiments, a consumer product or superabsorbent material comprises the superabsorbent polymer.

In some embodiments, a method of using a superabsorbent polymer comprises using the superabsorbent polymer in a consumer product or superabsorbent material.

In some embodiments, the consumer product is selected from the group consisting of cloth products, diapers, feminine napkins, and disposable bed liners.

EXAMPLES

Without further elaboration, it is believed that one skilled in the art using the preceding description can utilize the present invention to its fullest extent. The following Examples are, therefore, to be construed as merely illustrative, and not limiting of the disclosure in any way whatsoever.

Materials.

Unless otherwise indicated, the following materials were used in the examples: Acrylic acid (AA), 99%; Acrylamido-2-methylpropane sulfonic acid (AMPS), 99%; 2-(Methacryloloxy) ethyl] dimethyl-(3-sulfopropyl) ammonium hydroxide (DMAPS), 95%; Itaconic acid, 99%; 3-Sulfopropyl acrylate potassium salt (SPAK), 96%; 3-Sulfopropyl methacrylate potassium salt (SPMK), 98%; Potassium persulfate (KPS), ≥99%; N,N-Methylene(bis)acrylamide (MBAA), ≥99%; Ammonium persulfate (APS), ≥98%; N,N,N',N'-tetramethylethylenediamine (TEMED), ≥99.5%; 3-Sulfopropyl methacrylate potassium salt, 98%, 3-Sulfopropyl acrylate potassium salt, Poly (ethylene glycol) diacrylate (PEGDA), Mw=250 g/mol; Ethylene glycol dimethacrylate (EGDMA), Mw=198.22 g/mol; and Poly (ethylene glycol) dimethacrylate (PEGDMA), Mn=550 g/mol.

Comparative Example 1. Preparation of PAA-Based SAM Particles 16 g milli-Q water was added to a tall 200 mL reaction flask and 1.94 g 97% NaOH pellets for 70% neutralization (or 2.08 g in case of 75% neutralization) were dissolved in an ice bath. 5 g AA was added to the NaOH solution. 30 mg >99% MBAA was dissolved in 3 mL water and added to the above solution. The solution was stirred with a magnetic stir bar to ensure complete mixing. The reaction flask was purged with $N_2$ gas for 10 mins and the temperature was increased to 40° C. 15 mg APS, the redox initiator, was dissolved in 1 mL water and added to the reaction mixture with 10 μL TEMED. The reaction flask was sealed and kept under a low flow of $N_2$. Gelation started in 10-20 min. After gelation the reaction proceeded for 4 more hours. The geled reaction product was cut into small pieces and dried at 85° C. for 48 hours. The dried sample was ground using a coffee grinder. The dried gel particle size fraction between 300-600 microns was separated using appropriate sieves and dried overnight.

Comparative Example 2. Preparation of AMPS-Based SAM Particles 16 g milli-Q water was added to a tall 200 mL reaction flask and 2.08 g of 97% NaOH pellets was dissolved in the water, on an ice bath. 14.3 g of AMPS was added and completely dissolved in the reaction mixture. 30 mg of >99% MBAA was completely dissolved in 3 mL water and added to the above solution. The solution was stirred with a magnetic stirrer at about 300 rpm throughout the reaction. The pH of the reaction was measured and adjusted to around 4.8-5 by dropwise addition of 12 M NaOH solution. The reaction flask was purged with $N_2$ gas for 10 mins and temperature was increased to 40° C. 15 mg APS, the redox initiator, was dissolved in 1 mL water and added to the reaction mixture along with 10 µL TEMED. The reaction flask was sealed and kept under a low flow of $N_2$. Gelation started in 10-15 min. After gelation the reaction proceeded for 4 more hours. The geled reaction product was cut into the small pieces and dried in the oven at 85° C. for 48 hours. The dried sample was ground using a coffee grinder. The dried gel particle size fraction between 300-600 microns was separated using appropriate sieves and dried overnight.

Example 1. Preparation of AA 90%-AMPS 10%-Based SAM Particles 16 g milli-Q water was added to a tall 200 mL reaction flask. 2.08 g of 97% NaOH pellets was dissolved in the water, on an ice bath. 4.5 g AA (anhydrous, containing 200 ppm MEHQ as inhibitor, 99%) was added to the NaOH solution. 1.43 g of AMPS was then added and completely dissolved in the reaction mixture. 30 mg of >99% MBAA was completely dissolved in 3 mL water and added to the above solution. The solution was stirred with a magnetic stirrer throughout the reaction. The reaction flask was purged with $N_2$ gas for 10 mins and the temperature was increased to 40° C. 15 mg APS, the redox initiator, was dissolved in 1 mL water and added to the reaction mixture along with 10 µL TEMED. The reaction flask was sealed and kept under a low flow of $N_2$. Gelation started in 10-20 min. After gelation the reaction proceeded for 4 more hours. The geled reaction product was cut into small pieces and dried in the oven at 85° C. for 48 hours. The dried sample was ground using a coffee grinder. The dried gel particle size fraction between 300-600 microns was separated using appropriate sieves and dried overnight.

Example 2. Preparation of AA 90%-SPAK 10%-Based SAM Particles 16 g milli-Q water was added to a tall 200 mL reaction flask. 1.87 g of 97% NaOH pellets was dissolved in water on an ice bath. 4.5 g AA was added to the NaOH solution. 1.60 g of SPAK was then added and completely dissolved in the reaction mixture. 30 mg of >99% MBAA was completely dissolved in 3 mL water and added to the above solution. The solution was stirred with a magnetic stirrer throughout the reaction. The reaction flask was purged with $N_2$ gas for 10 mins and the temperature was increased to 40° C. 15 mg APS, the redox initiator, was dissolved in 1 mL water and added to the reaction mixture along with 10 µL TEMED. The reaction flask was sealed and kept under a low flow of $N_2$. Gelation started in 10-20 min. Ater gelation the reaction proceeded for 4 more hours. The geled reaction product was cut into small pieces and dried in the oven at 85° C. for 48 hours. The dried sample was ground using a coffee grinder. The dried gel particle size fraction between 300-600 microns was separated using appropriate sieves and dried overnight.

Example 3. Preparation of AA 90%-SPMK 10%-Based SAM Particles 16 g milli-Q water was added to a tall 200 mL reaction flask. 1.87 g of 97% NaOH pellets was dissolved in water on an ice bath. 4.5 g AA was added to the NaOH solution. 1.70 g of SPMK was then added and completely dissolved in the reaction mixture. 30 mg of >99% MBAA was completely dissolved in 3 mL water and added to the above solution. The solution was stirred with a magnetic stirrer throughout the reaction. The reaction flask was purged with $N_2$ gas for 10 mins and the temperature was increased to 40° C. 15 mg APS, the redox initiator, was dissolved in 1 mL water and added to the reaction mixture along with 10 µL TEMED. The reaction flask was sealed and kept under a low flow of $N_2$. Gelation started in 10-20 min. After gelation the reaction proceeded for 4 more hours. The geled reaction product was cut into small pieces and dried in the oven at 85° C. for 48 hours. The dried sample was ground using a coffee grinder. The dried gel particle size fraction between 300-600 microns was separated using appropriate sieves and dried overnight.

Example 4. AUL Measurements of SAM Particles

AUL measures the ability of a polymer to absorb fluid under a static load and can be considered as a measurement of gel swelling coupled with gel strength. A typical AUL test format was used, consisting of a simple cylindrical device with a macro-porous sintered filter plate at one end of a sintered plastic cylinder. For the samples tested, 160 mg ($W_1$) of the dried SAP sample was weighed and evenly placed on the surface of polyester gauze placed on top of the sintered plastic. The desired load (0.3, 0.6, or 0.9 PSI) was then placed on top of the dry SAP particles, with the load designed so it can freely move in the plastic cylinder. The device was placed in a petri dish of 0.9% saline solution on the top of a mesh (to ensure that water can access the bottom of the sintered plastic) for 1 hour. The swollen sample was weighed ($W_2$), and the AUL was calculated using Equation (1)

$$AUL\left(\frac{g}{g}\right) = \frac{W2 - W1}{W1}. \quad (1)$$

About 0.160 g of each type of SAM particles prepared according to Comparative Example 1, Comparative Example 2, Example 1, Example 2, and Example 3 were placed into an AUL measurement cup and covered with a lid and a steel cylinder weighing 100 g. The pressure on SAM particles was 0.3 PSI. The cups were placed into 0.9% saline for 1 hour. The absorbed water was weighed for each cup. AUL was then calculated by dividing the absorbed water by SAM particle weight. The average 1 hour AUL of AA-based SAMs was 12.4. The average 1 hour AUL for AA/AMPS (87.5%/12.5%) was 15.4. The average 1 hour AUL for AMPS-based SAM particles was 11.5.

These results demonstrate the improved AUL of SAM particles based on copolymers of AA/AMPS compared to SAM particles based solely on AA and SAM particles based solely on AMPS.

Example 5. Syntheses of Copolymer Compositions

A variety of new copolymer compositions were synthesized primarily by replacing a fraction of the AA (5, 10, 15, 20, 25 or 30 mole % of the total monomers present in the backbone) with different monomers to make copolymer hydrogels using a free radical copolymerization reaction in water. Unless otherwise stated, the acrylic acid was partially neutralized (70%), N,N'-methylene(bis)acrylamide (99% purity) was used as the crosslinker (0.21-0.23 mol % to total monomer) and potassium persulfate (≥99.0% purity) was used as the thermal initiator (0.08-0.1 mol % to total monomer).

Each polymerization reaction was carried out according to the following procedure. A 200 mL glass beaker was immersed in an ice bath. NaOH pellets were dissolved in milli-Q water, and acrylic acid was added. For each series of reactions, a stock solution of defined concentration of crosslinker (10 mg/ml) and initiator (20 mg/ml) were made freshly prior to each synthesis. The desired amounts of crosslinker was added to each reaction mixture, after which the mixture was purged with nitrogen for 5-10 minutes and temperature was increased. The beaker was sealed and kept under a low flow of nitrogen to ensure inert conditions throughout the polymerization. The reaction was allowed to proceed for about 4 hours, although macroscopic gelation was observed for most of the samples within 10-15 minutes. The prepared gels were cut into smaller pieces and dried in an oven at 85° C. for 48 hours. The dried gel was ground and sieved, with all particles used for subsequent testing collected between a 600 µm and a 300 µm standard sieve.

Specific motivations for the selected comonomers and details of the respective syntheses follow.

AMPS

Although AMPS has an acrylamide-based backbone structure and thus does not copolymerize fully randomly with AA, the monomer is an inexpensive and commercially available hydrophilic, sulfonic acid-based monomer that has a permanent charge at pH1 values well below physiological pH, providing a high degree of hydrophilicity and anionic character over a wide range of pH. The side chain also contains an anionic charge in aqueous conditions that is spaced further away from the backbone and is thus less likely to significantly influence the degree of ionization of neighboring acrylic acid residues, in which the charged residues are much closer to the polymer backbone.

Hydrogels were prepared using the general conditions described above. As AMPS is a strong acid, the amount of necessary NaOH to achieve 70% or 75% total ionization (AMPS+AA, corresponding to all AMPS and a fraction of the residual AA based on the $pK_a$s of the two monomers) was calculated. After completely dissolving the NaOH pellets and acrylic acid in water, AMPS was added to the neutralized mixture. The gelation happened in less than 10 minutes, although the reaction was continued for 4 more hours. All the prepared gels appeared clear and were neither sticky nor excessively brittle. The gels remained clear upon drying, although a slight yellowish color was observed which disappeared upon rehydration of the gels.

SPAK

3-Sulfopropyl acrylate potassium salt (SPAK) is an acrylate monomer with a sulfate group tethered away from the polymer backbone that copolymerizes easily with acrylic acid and, given its similar polymerizable group, is likely to result in copolymers with AA that possess a high degree of randomness.

Hydrogels were prepared using the general conditions described above, calculating the neutralization degree as described for AMPS. Gelation happened in 10-15 minutes, although the reaction was continued for 4 more hours. All the prepared gels appeared clear and were neither sticky nor excessively brittle. The gels remained clear upon drying, although a slight yellowish color was observed that disappeared upon rehydration of the gels.

SPMK

3-Sulfopropyl methacrylate potassium salt (SPMK) has the same spacer and tethered sulfate group as SPAK, but has a polymerizable methacrylate group instead of an acrylate group. As such, while SPMK can readily copolymerize with acrylic acid, the backbone will be somewhat sterically hindered and the polymerizable group of the monomer is likely to react at a different rate than AA. This difference is likely to result in less random copolymers with AA but the same tethering distance of the sulfate group from the polymer backbone compared to SPAK.

Hydrogels were prepared using the general conditions described above, calculating the neutralization degree as described for AMPS. Gelation happened in 10-15 minutes, although the reaction was continued for 4 more hours. All the prepared gels appeared clear and were neither sticky nor excessively brittle. The gels remained clear upon drying, although a slight yellowish color was observed that disappeared upon rehydration of the gels.

DMAPS

Sulfobetaines are an important class of zwitterionic structures that contain a quaternary ammonium and a sulfonate group. Due to the presence of these positively and negatively charged groups within the same repeating units, sulfobetaine hydrogels can maintain a constant near net-zero charge irrespective of the pH of the medium. Sulfobetaine monomers also bind an extremely large amount of water (up to 14 water molecules per repeat residue), a high water binding state that persists even in high ionic strength media like urine or blood.

Hydrogels were prepared using the general conditions described above. Gelation was observed in all samples in less than 15 minutes. The appearance of the prepared gels was clear. During the drying process, the gels shrank and became slightly yellow in appearance but remained clear. The dried gels were ground very easily, with a high percentage of fine particles observed.

VSA

Vinyl sulfonic acid is a highly reactive unsaturated sulfonic acid. It is a colorless, water-soluble liquid, although commercial samples can appear yellow or even red. Polyvinyl sulfonic acid (PVSA; as sodium salt) is a blood-compatible polyelectrolyte that has negatively charged sulfonate groups. Relative to AMPS, the anionic functional group (again fully charged at physiological pH) is significantly closer to the polymer backbone, at a similar distance to the —COOH groups in AA residues. Thus, this monomer was chosen to assess any differences in swelling observed depending on how far away from the backbone the charged group is tethered.

Hydrogels were prepared using the general conditions described above. Gelation occurred quickly (within about 15 minutes) to create clear but extremely sticky gels that were difficult to remove from the beaker. During the drying process, the gels remained sticky and turned slightly yellow while remaining clear. Based on their sticky nature, the gels were also difficult to grind.

Example 6. AUL and CRC Results of Copolymer Compositions

The swelling results, namely absorption under load (AUL) and centrifuge retention capacity (CRC), for the copolymer compositions prepared according to Example 3 are presented in Table 1. These copolymer compositions were prepared with different functional co-monomers (initiator: KPS, temperature: 70° C.). Incorporated monomers include acrylic acid (AA), 2-acrylamido-2-methylpropane sulfonic acid (AMPS), 3-Sulfopropyl acrylate potassium salt (SPAK), 3-Sulfopropyl methacrylate potassium salt (SPMK), [2-(Methacryloyloxy)ethyl]dimethyl-(3-sulfopropyl)ammonium hydroxide (DMAPS), and vinyl sulfonic acid (VSA).

AUL was measured according to the procedures of Example 4.

In contrast to AUL testing, in which a dry powder of SAP is hydrated under load, a CRC test measures the capacity of a pre-swollen SAP to retain water under force. To perform the test, about 100 mg ($W_2$) of the dried SAP sample was weighed into a pre-weighed tea bag. The tea bag was immersed in 0.9 saline solution for 1 hour to swell the SAP. Subsequently, the tea bag was placed inside a cylindrical centrifuge tube containing a porous inside to allow for water drainage and centrifuged for 3 minutes at 1600 rpm. As a control, an empty tea bag also was put in saline and centrifuged at the same speed. After centrifugation, the tea bag was weighed again ($W_2$), and the difference between the dried and swollen sample was calculated. The CRC amount was calculated by Equation (2):

$$CRC\left(\frac{g}{g}\right) = \frac{W2 - W1}{W1}. \quad (2)$$

All AUL measurements reported represent averages of 2-3 repeat measurements per batch. In cases where more than one AUL number is reported, the second number represents an independent replicate batch. CRC was measured using 100 g weights.

TABLE 1

AUL and CRC results for copolymer superabsorbent hydrogels prepared with different functional co-monomers.

| Copolymer | AUL (g/g) 0.3 PSI | % Change vs control | CRC (g/g) | % Change vs control |
| --- | --- | --- | --- | --- |
| AA control | 12.5 | | 40.2 | |
| | 13.0 | | 38.0 | |
| | 12.8 | | 39.0 | |
| AA 90%/AMPS 10% | 14.5 | 13 | 32 | −17 |
| AA 85%/AMPS 15% | 15 | 17 | 31 | −20 |
| AA 87.5%/AMPS 12.5% | 15.6 | 22 | 34.8 | −10 |
| AA 82.5%/AMPS 17.5% | 16.5 | 29 | 33.5 | −14 |
| AA 90%/SPAK 10% | 16 | 25 | 32 | −18 |
| AA 85%/SPAK 15% | 17.6 | 38 | 30 | −23 |
| AA 90%/SPMK 10% | 16.5 | 29 | 33 | −15 |
| AA 85%/SPMK 15% | 16 | 15 | 32 | −18 |
| AA 90%/DMAPS 10% | 10 | −21 | 32.2 | −18 |
| AA 85%/DMAPS 15% | 8 | −37 | 33.8 | −14 |
| AA 80%/DMAPS 20% | 7.5 | −42 | 31.4 | −19 |
| AA 90%/VSA 10% | 12.5-10.2 | −13 | 35.6 | −10 |
| AA 85%/VSA 15% | 11.0-9.0 | −19 | 36 | −10 |

The swelling results indicate an increase in AUL using most of the synthesized copolymers in comparison to the control hydrogels. This result clearly indicates the benefits of copolymerizing monomers that have different types of charges (in particular AMPS, SPAK, and SPMK) into AA-based SAPs. SPAK and SPMK can yield hydrogels with particularly high AUL values that are up to 38% higher than those achieved with the AA-only control.

Copolymerization appears to reduce the CRC of most hydrogels, with most copolymers resulting in CRC decreases in the order of 10-25%. This opposite trending of CRC and AUL is consistent with conventional observations, although minimizing this CRC reduction is desirable. However, certain compositions (e.g. AA 87.5%/AMPS 12.5% with a crosslinker content of 0.31 mol % and AA 82.5%/AMPS 17.5% with a crosslinker content of 0.31 mol %) show relatively minimal decreases in CRC (about 10-15%) while still demonstrating greater than 20% improvements in AUL.

Mixing methacrylate monomers with tethered sulfate groups (AMPS, SPAK, SPMK) with AA is a promising strategy for increasing AUL, while introducing a vinylic sulfate monomer in which the charge is close to the main chain (VSA) resulted in similar or slightly reduced AULs accompanied by significantly reduced CRCs. Thus, either the backbone structure of the monomer or the distance between the backbone and the charged sulfate group substantially changes the performance of the SAP.

Copolymerization of the zwitterionic monomer DMAPS does not appear to give a significant benefit over the AA control.

Incorporating AMPS into the hydrogel consistently increases the AUL measured versus any relevant AA control.

Example 7. Effect of Crosslinker Length

In order to evaluate the effect of the length of the crosslinker on SAP performance, the performance of hydrogels prepared with PEG diacrylate-based crosslinkers with various PEG chain lengths was analyzed for AA-co-AMPS copolymers. AA-only controls were also prepared using the same crosslinker types/amounts to enable direct comparisons of the observed swelling responses.

Hydrogels were prepared using the same protocols typically used for each comonomer mixture but substituting the MBAA content with the same molar ratio of PEGDA, EGDMA, or PEGDMA. Gelation occurred in a few minutes to create clear gels, although hydrogels crosslinked by EGDMA and PEGDMA were somewhat stickier than the controls.

It was determined that higher AUL values can be achieved by using higher crosslink densities. However, consistently substantial AULs are observed at degrees of neutralization of 70%, 75%, or 80%. This relative independence of the degree of neutralization is a process-related benefit to using the AMPS copolymerization approach for formulating SAPs, as AA-only hydrogels are more sensitive to the degree of neutralization of the reaction mixture.

Example 8. Incorporation of Multiple Charges on the Same Monomer

To assess the potential of incorporating two anionic charges on the same monomer unit, itaconic acid (IA) copolymers were assessed for AA and AA-co-AMPS. The resulting AUL and CRC performances of the IA-incorporated hydrogels are shown in Table 2.

TABLE 2

Performance of copolymers incorporating two anionic charges.

| Copolymer | Crosslinker | AUL (g/g) 0.3 PSI | CRC (g/g) |
| --- | --- | --- | --- |
| AA control | PEGDA | 13 | 39 |
| AA 80%/AMPS 20% | PEGDA | 13.3 | 35 |

TABLE 2-continued

Performance of copolymers incorporating two anionic charges.

| Copolymer | Crosslinker | AUL (g/g) 0.3 PSI | CRC (g/g) |
|---|---|---|---|
| AA 90%/IA 10% | PEGDA | 10.8 | 33 |
| AA 90%/IA 10% | MBAA | N/A | N/A |
| AA 80%/IA 20% | MBAA | N/A | N/A |

IA cannot crosslink by with MBAA under the same conditions as AA. Homopolymerization of IA is hindered by the allylic hydrogen atoms within IA that can act as chain transfer agents, with the rate of copolymerization of IA being strongly dependent on both the pH and the degree of ionization of IA. However, by switching the crosslinker to PEGDA, gelation could be achieved. The resulting gels were significantly stickier than the AA-only or AA-co-AMPS control gels and showed substantially reduced AUL values versus either gel, although the CRCs achieved are substantially higher.

The results herein demonstrate that copolymerization of monomers with different types of charges significantly change the absorbency of AA-based hydrogels. Copolymer hydrogels of AA and AMPS show the best combination of good performance (significantly higher AUL and matched CRC compared to relevant control) and ease of synthesis.

This written description uses examples to illustrate the present disclosure, including the best mode, and also to enable any person skilled in the art to practice the disclosure, including making and using any compositions or systems and performing any incorporated methods. The patentable scope of the disclosure is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

As used herein, the terms "comprises." "comprising," "includes," "including," "has," "having." "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where an invention or a portion thereof is defined with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "about" means plus or minus 10% of the value.

What is claimed is:

1. A superabsorbent polymer comprising
    a copolymer comprising
        a major portion of low molecular weight monomers each individually comprising a backbone and a charged moiety;
        a minor portion of high molecular weight monomers each individually comprising a backbone and a charged moiety; and
    optionally a crosslinker;
    wherein an average distance between the backbone and charged moiety of each individual low molecular weight monomer is less than an average distance between the backbone and charged moiety of each individual high molecular weight monomer;
    wherein the copolymer lacks structured ordering of the low molecular weight monomers and the high molecular weight monomers.

2. The superabsorbent polymer of claim 1, wherein the major portion is present in an amount greater than about 60 mol % of the copolymer and the minor portion is present in an amount less than about 40 mol % of the copolymer.

3. The superabsorbent polymer of claim 1, wherein the superabsorbent polymer is in a form selected from the group consisting of a particle, a gel, a fiber, a bead, a liquid, a solid, a paste, and combinations thereof.

4. The superabsorbent polymer of claim 1, wherein the superabsorbent polymer is in the form of a particle with a diameter in the range of about 100 µm to about 1000 µm.

5. The superabsorbent polymer of claim 1, wherein the superabsorbent polymer is surface-crosslinked.

6. The superabsorbent polymer of claim 1, wherein the crosslinker density is in the range of about 0.05 mol % to about 1 mol %.

7. The superabsorbent polymer of claim 1, wherein the average distance between the backbone and charged moiety of each individual low molecular weight monomer is less than about 5 angstroms and the average distance between the backbone and charged moiety of each individual high molecular weight monomer is greater than about 5 angstroms.

8. The superabsorbent polymer of claim 1, wherein each individual low molecular weight monomer has a molecular weight less than about 150 g/mol and each individual high molecular weight monomer has a molecular weight greater than about 150 g/mol.

9. The superabsorbent polymer of claim 1, wherein each individual high molecular weight monomer is selected from the group consisting of 2-acrylamido-2-methylpropane sulfonic acid, 3-sulfopropyl methacrylate, 3-sulfopropyl acrylate, acrylate or methacrylate monomers with tethered sulfate groups and salts thereof, salts of vinyl-linker-acid units, and vinylic sulfate monomers.

10. The superabsorbent polymer of claim 1, wherein each individual low molecular weight monomer is selected from the group consisting of acrylic acids, methacrylic acids, vinyl sulfonic acids, vinyl phosphoric acids, partially hydrolyzed maleic anhydrides, and combinations thereof.

* * * * *